(12) United States Patent
Taylor et al.

(10) Patent No.: US 9,981,092 B2
(45) Date of Patent: May 29, 2018

(54) PRESSURISED METERED DOSE INHALERS AND METHOD OF MANUFACTURE

(71) Applicant: CARDIFF SCINTIGRAPHICS LIMITED, Cardiff (GB)

(72) Inventors: Glyn Taylor, South Glamorgan (GB); Simon Warren, South Glamorgan (GB); Cuong Tran, South Glamorgan (GB)

(73) Assignee: CARDIFF SCINTIGRAPHICS LIMITED, Heath Park, Cardiff (GB)

( * ) Notice: Subject to any disclaimer, the term of this patent is extended or adjusted under 35 U.S.C. 154(b) by 0 days. days.

(21) Appl. No.: 15/117,549

(22) PCT Filed: Feb. 12, 2015

(86) PCT No.: PCT/GB2015/050390
§ 371 (c)(1),
(2) Date: Aug. 9, 2016

(87) PCT Pub. No.: WO2015/121653
PCT Pub. Date: Aug. 20, 2015

(65) Prior Publication Data
US 2016/0354564 A1    Dec. 8, 2016

(30) Foreign Application Priority Data

Feb. 13, 2014 (GB) .................................. 1402513.4

(51) Int. Cl.
| | |
|---|---|
| *A61K 9/00* | (2006.01) |
| *A61K 9/20* | (2006.01) |
| *A61M 15/00* | (2006.01) |
| *A61K 9/28* | (2006.01) |
| *B65B 31/00* | (2006.01) |
| *B65B 63/02* | (2006.01) |

(52) U.S. Cl.
CPC ........... *A61M 15/009* (2013.01); *A61K 9/008* (2013.01); *A61K 9/0073* (2013.01); *A61K 9/205* (2013.01); *A61K 9/2009* (2013.01); *A61K 9/2013* (2013.01); *A61K 9/2018* (2013.01); *A61K 9/2027* (2013.01); *A61K 9/2063* (2013.01); *A61K 9/282* (2013.01); *A61K 9/284* (2013.01); *A61K 9/2853* (2013.01); *B65B 31/003* (2013.01); *B65B 63/02* (2013.01); *A61M 2207/00* (2013.01)

(58) Field of Classification Search
None
See application file for complete search history.

(56) References Cited

U.S. PATENT DOCUMENTS

| | | | |
|---|---|---|---|
| 5,776,432 A | | 7/1998 | Schultz et al. |
| 6,123,924 A | | 9/2000 | Mistry |
| 6,455,028 B1 | * | 9/2002 | Wulffhart ............... A61K 9/008 424/434 |
| 2005/0129621 A1 | * | 6/2005 | Davies ................... A61K 9/008 424/45 |

FOREIGN PATENT DOCUMENTS

| | | |
|---|---|---|
| EP | 2062572 A1 | 5/2009 |
| WO | 91/04011 A1 | 4/1991 |
| WO | 1998056349 A1 | 12/1998 |
| WO | 1999051205 A1 | 10/1999 |
| WO | 2008053250 A2 | 5/2008 |
| WO | 2009/013213 A2 | 1/2009 |
| WO | 2011/098798 A1 | 8/2011 |
| WO | 2011/112922 A2 | 9/2011 |

OTHER PUBLICATIONS

PCT/GB2015/050390—International Search Report and Written Opinion of the International Searching Authority dated May 18, 2015.
UK IPO Search Report for GB1402513A dated Aug. 21, 2014.

* cited by examiner

*Primary Examiner* — Robert T. Crow
*Assistant Examiner* — John P Nguyen
(74) *Attorney, Agent, or Firm* — King & Schickli, PLLC (57) ABSTRACT

The invention relates to a method for the manufacture of a pressurized Metered Dose Inhaler (pMDI) and components for use in said method, in particular, a pMDI compatible tablet (i.e. one that is able to be dispersed or disintegrates within a liquid phase, such as a propellant, used in a pMDI formulation) which contains at least one active pharmaceutical ingredient (API) and, optionally, one or more excipients.

27 Claims, 1 Drawing Sheet

PRESSURISED METERED DOSE INHALERS AND METHOD OF MANUFACTURE

This application is the national stage of international patent application no. PCT/GB2015/050390 filed on Feb. 12, 2015 which in turn claims priority from British Patent Application No. 1402513.4 filed on Feb. 13, 2014, the disclosures of which are incorporated herein by reference in their entirety.

TECHNICAL FIELD

The invention relates to a method for the manufacture of a pressurised Metered Dose Inhaler (pMDI) and components for use in said method, in particular, a pMDI compatible tablet (i.e. one that is able to be dispersed or disintegrates within a liquid phase, such as a propellant, used in a pMDI formulation) which contains at least one active pharmaceutical ingredient (API) and, optionally, one or more excipients.

BACKGROUND

The key component of a pMDI is a canister which contains a liquid phase such as a propellant (which may also include low volatility co-solvents) in which the active pharmaceutical ingredient (API) is present either in solution or suspended in the form of micronised particles (either micrometers or nanometers in diameter). The propellants commonly used are hydrofluoroalkanes (HFA) such as HFA 134a (tetrafluorethane) and HFA 227ea (heptafluoropropane). Solvents of relatively low volatility e.g. ethanol, and/or formulation modifiers e.g. glycerol are often included in the formulations to enhance API solubility in the propellant to yield a solution formulation, or to modify the aerosol properties of the formulation (1, 2). Many APIs or drugs however do not have sufficient solubility in HFA/solvent blends or, alternatively, are not chemically stable in solution and as a result suspension systems must be formulated. Low volatility solvents are also used in suspension systems to promote the solubility of surfactants which function to stabilize the suspension of micronised API particles. pMDIs are the most commonly used delivery systems for treating asthma, chronic obstructive pulmonary disease (COPD) and other diseases of the respiratory tract and for administering to the buccal cavity.

The pMDI container (usually in the form of an aluminium canister which may be anodized or coated, or a stainless steel canister) provides a reservoir for doses, typically between 60 to 200 metered doses, which will usually provide one months' medication for a patient, or may provide one dose of a rescue medication. The doses are dispensed via a metering valve which is crimped onto the pMDI container. Typical metered volumes range from 25-75 µL. In use, the canister is housed in a plastic actuator which enables the metered volume to be delivered as an aerosol to the patient via the actuator mouthpiece.

Manufacturing processes fall broadly into two categories; single stage filling or two-stage filling. In the former process the formulation consists of an API, or combination of APIs, either suspended or dissolved in the propellant (which may also contain a small fraction of low volatility solvent e.g. ethanol and an appropriate surfactant). During manufacture the propellant is maintained as a liquid by the use of high pressure or low temperature. In the case of a suspension formulation the micronised API (ideal particle size in the region of 3 µm) must be homogenously dispersed during all stages of manufacture and care is taken to ensure that the particulate API does not settle or aggregate in any of the vessels, homogenisers, pumps, machinery or filling lines required to dispense the formulation into the pMDI container. Very often it is necessary to continuously homogenise and recirculate the liquefied suspension formulation to ensure uniform dispersion of the API. During filling care must be taken to ensure accurate and reproducible filling of API/propellant into the pMDI container. Filling may be performed into open canisters followed by crimping on of the metering valve (cold filling) or alternatively the API/propellant may be dispensed into the sealed cans via the metering valve (pressure filling).

For two-stage filling, the "first stage" typically involves dispensing of a concentrated suspension or solution of API in a low volatility solvent or suspending medium e.g. ethanol (with or without appropriate surfactant) into an open pMDI container followed by crimping on of the metering valve. Care must be taken to ensure that the filling procedure delivers an accurate and reproducible amount of API solution or suspension into every container and very often it is necessary to continuously homogenise and recirculate formulations to ensure uniform dispersion of the API. The "second stage" involves the addition of an accurate and reproducible amount of propellant.

One of the inventors has previously shown (3) that effective formulations for suspension pMDIs may include a (second) particulate material (excipient) in addition to the micronised API within the liquid propellant. The particle size distribution of the second particulate is predominantly greater than that of the micronised API. The particulate carrier and the API may be present as either a simple admixture or with some or all of the smaller API particles interacting with the larger particles of the second particulate material.

However, in contrast to this earlier work it is herein disclosed a new pMDI formulation and a process for the manufacturing of a pMDI, wherein the API is added to a canister in tablet form prior to the processes of (in the order consistent with pressure or low temperature filling) crimping the metering valve on the canister and filling with propellant.

There is therefore disclosed herein the production of a pMDI using at least one API(s) in the form of a tablet wherein the API is either on its own or with at least one excipient.

SUMMARY

According to a first aspect of the invention there is provided a method for the manufacture of a pMDI comprising:
i) compressing a selected amount of:
at least one particulate active pharmaceutical ingredient (API) into a tablet;
ii) placing said tablet into a canister;
iii) fixedly attaching a dispensing valve to said canister; and
iv) dispensing liquid phase into said canister.

Whilst the above method is presented as a single process, there may be an interval following steps i), ii) or iii. Moreover step iv) may occur before step iii) as appropriate for low temperature filling. Thus the various steps may be undertaken as part of a single sequential manufacturing process or the various steps may be undertaken, sequentially, but after time intervals typically determined by convenience and also, possibly, the steps may be undertaken in different environments. Indeed, it is the devising of the invention that lends itself to the fragmentation (discontinuity) of the manufacturing process whereby component parts of pMDIs can be manufactured.

Reference herein to tablet refers to a compacted dosage form of the API, with or without suitable excipients/diluents, produced by compression or compaction of same.

As will be appreciated by those skilled in the art, said tablet may vary in shape, size, weight and density, whilst still achieving the desired technical effect as disclosed herein.

The invention offers a number of potential advantages over the pMDI manufacturing processes described in the background, these advantages are described within the invention and claims below.

In a preferred embodiment of the invention said API is micronised.

In yet a further preferred embodiment of the invention said API is soluble in a liquid phase. Hereinafter, liquid phase shall include but is not limited to propellant such as HFA propellant (which may contain a blend of HFA propellants, and optionally a proportion of suitable hydrocarbon(s) and/or low volatility co-solvents, and/or formulation modifiers). Preferably said soluble APIs include but are not limited to beclometasone dipropionate or ciclesonide or formoterol fumarate dihydrate or ipratropium, or flunisolide hemihydrate.

Alternatively, or additionally, said API is insoluble in the liquid phase. Preferably said insoluble APIs are selected from but are not limited to the group comprising: salbutamol sulphate, fluticasone propionate or salmeterol xinafoate.

In addition, either in solution or suspension form, the following APIs could be formulated with this invention: bronchodilators, e.g., indacaterol maleate, olodaterol, vilanterol, ephedrine, adrenaline, fenoterol, isoprenaline, metaproterenol, phenylephrine, phenylpropanolamine, pirbuterol, reproterol, rimiterol, terbutaline, isoetharine, tulobuterol; anti-inflammatories, e.g. budesonide, rofleponide, mometasone furoate or triamcinolone acetonide anticholinergics, e.g., tiotropium, aclidinium bromide, glycopyrronium bromide, umeclidinium, atropine or oxitropium; xanthines, e.g. theophylline.

Further examples of appropriate APIs may additionally be selected from, for example, analgesics, e.g. codeine, dihydromorphine, ergotamine, fentanyl or morphine; anginal preparations, e.g., diltiazem; antiallergics, e.g., cromoglycate, ketotifen or nedocromil; anti-infectives e.g., cephalosporins, penicillins, streptomycin, sulphonamides, tetracyclines and pentamidine; antihistamines, e.g., methapyrilene; antitussives, e.g., noscapine; diuretics, e.g., amiloride; hormones. e.g., cortisone, hydrocortisone or prednisolone: therapeutic proteins and peptides. e.g., insulin or glucagon, calcitonin, growth hormone, lutenising hormone release hormone (LHRH), leuprolide, oxytocin.

It will be clear to a person skilled in the art that, where appropriate, the APIs may be used in the form of salts, (e.g., as alkali metal or amine salts or as acid addition salts) or as esters (e.g., lower alkyl esters) or as solvates (e.g., hydrates) to optimise the activity and/or stability of the API.

In yet a further preferred embodiment of the invention, a disintegrant (something that disintegrates or disperses in the liquid phase) and/or excipient is compressed into said tablet.

In yet a further preferred embodiment of the invention said liquid phase comprises a low volatility solvent and/or a surfactant.

In a preferred embodiment of the invention a plurality of APIs may be used in the above method. Ideally, each will be selected having regard to the nature of the condition to be treated. More preferably, at least one or a plurality of APIs is/are soluble in the liquid phase or at least one or a plurality of APIs are insoluble in the liquid phase.

Alternatively, at least one API soluble in the liquid phase and at least one API insoluble in the liquid phase is used in the above method. As will be appreciated by those skilled in the art, advantageously, this permits manufacture of a pMDI having a combination of disparate APIs (soluble and insoluble) to be incorporated into the same canister, which conventionally has been problematical due to their different chemical states. Further, without wishing to be bound by theory, we consider that as the compressed soluble API will more readily dissolve and disperse, homogeneous dispersal of the insoluble API will occur more readily.

In a further preferred embodiment of the invention said disintegrant is selected on the basis that it has sufficient solubility in the liquid phase such that when exposed to same, the disintegrant dissolves and goes into solution resulting in the structure of the tablet breaking down and any insoluble API and any insoluble excipient (if included) is homogeneously dispersed in the liquid phase (which may contain a low volatility solvent and/or modifier e.g. surfactant). Alternatively if the API is sufficiently soluble in the liquid phase it may be dissolved along with the disintegrant and any insoluble excipient will then be dispersed in the liquid phase.

Accordingly, reference herein to a disintegrant is to a material that can be compressed into a tablet form with said API, and (when present) an excipient, and which is soluble in said liquid phase.

Those skilled in the art will therefore appreciate than its broadest teaching, the invention concerns the provision of one or more particulate active pharmaceutical ingredients (APIs) compressed into a tablet and used to work the afore method. More typically, the invention is worked using at least one API and a disintegrant and/or excipient.

Most preferably, said disintegrant is included in said tablet and is selected from the group comprising: menthol, propylene glycol (PG), polyvinylpolypyrrolidone (PVP), polyethylene glycol (PEG), glycerol, sodium bicarbonate, citric acid and non-toxic essential oils.

In yet a further preferred embodiment, the invention is worked using at least one API, a disintegrant and an excipient.

In yet a further preferred embodiment of the invention the method of part i) further includes compressing a lubricant/glidant such as, for example, magnesium stearate into said tablet.

Most preferably, said disintegrant is mixed with or coated onto said one or more API's then this material is compressed into said tablet. Additionally, or alternatively, said disintegrant is mixed with or coated onto said excipient (when present) then this material is compressed into said tablet with said API. Said tablet is then exposed to said liquid phase in which it dissolves and/or is dispersed leaving a solution or dispersion of API or API/excipient and solubilised disintegrant.

Most preferably still, said disintegrant is a non-toxic essential oil i.e. it is an oil extracted from plant material or its corresponding synthetic counterpart such as the oil extract from allspice, amber, anise, arnica, basil, bay bergamot, rose wood, cajeput, calendula, camphor, caraway, cardamom, carrot, cedar, celery, chamomile, cinnamon, citronella, clary sage, coriander, cumin, cypress, eucalyptus, fennel, fir, frankincense, garlic, geranium. Ginger, grapefruit, hissop, jasmine, jojoba, juniper, lavender, lemon, lemongrass, lime marjoram, menthol, mugwort, mullein, myrrh, neroli, nutmeg, orange, oregano, patchouly, pepper, peppermint, pine, rose, rosehip, rosemary, sage, sandalwood, spearmint, tangerine, tea tree, thyme, vanilla, vetivert, witch hazel, and ylang ylang. Notably, these essential oils show good solubility in HFA propellants (4). Preferably said essential oils are used at a concentration range less than 1% to 20% w/w in liquid propellant.

In a preferred embodiment of the invention said excipient is a particulate carrier material. Preferred materials include those commonly used in pharmaceutical drug delivery systems, e.g. carbohydrates including sugars, mono-, di-, tri-, oligo-, polysaccharides and any physiologically acceptable derivatives, salts, solvates thereof and any mixtures thereof e.g. lactose, spray dried lactose. Other suitable particulate carrier materials include amino acids, di-, tri-, oligo-, polypeptides, proteins and any physiologically acceptable derivatives, salts, solvates thereof and mixtures thereof, e.g. leucine. Advantageously, because of their relatively large particle size (i.e. range 15 μm-200 μm) these carrier particles are not likely to penetrate into the lungs during use. Thus, preferred particulate carrier materials have a particle size in the range 15 μm-200 μm.

More preferably, said excipient is coated with a disintegrant selected from the group comprising: menthol, propylene glycol (PG), polyvinylpolypyrrolidone (PVP), polyethylene glycol (PEG), glycerol, sodium bicarbonate, citric acid and a non-toxic essential oil.

We have discovered that upon addition of the liquid phase to the canister the tablet, and any disintegrant and/or excipient, may be effectively disintegrated by the energy imparted as the liquid phase fills the canister. In some instances, agitation or sonication may be additionally required to completely effect disintegration or dispersion. After tablet disintegration or dispersion the API and any disintegrant and/or excipient/particulate carrier exist dissolved/suspended in the liquid phase. Thus the amount of disintegrant added to the tablet is ideally the minimum required to ensure the necessary dispersion of the tablet upon contact with the liquid phase.

In a preferred method the propellant is a hydrofluorcarbon and mixtures or blends thereof. Preferably said propellant is a hydrofluoroalkane (HFA) such as e.g. HFA 134a (tetrafluorethane) or HFA 227ea (heptafluoropropane) and or blends mixtures thereof. Preferably said propellant is a hydrofluoroolefin and mixtures or blends thereof.

In a further preferred embodiment of the invention said afore propellants also contain low volatility solvents e.g. ethanol and/or appropriate surfactants and may also contain appropriate proportions of selected hydrocarbons and/or formulation modifiers.

In a further preferred method of the invention said propellant comprises at least 80% w/w and up to 99.99% w/w, more preferably at least 90% w/w and up to 99.9% w/w).

As mentioned, we have also discovered that having the API provided as a tablet gives flexibility to the manufacture of the finished product. This is because the tablet formulations, if stored appropriately, possess pharmaceutical stability so that dispensing same into canisters could, if necessary, be performed a significant length of time after preparing the tablets. Thus the tablets could be dispensed into canisters and valves fixedly attached, typically by crimping, at one facility followed by the addition of the propellant at another facility. The final manufacturing site would not therefore require costly and complex pressure mixing vessels for dispensing pressurised suspensions. Moreover, exposure to open sources of the API would be restricted to one site.

Other advantages that flow from the above manufacturing process arise from the avoidance of having to undertake real time API analytical in-process controls to determine the quantity of API dispensed into each container. Indeed, this measuring could be performed during tablet manufacture using well establish methodologies. Furthermore, there would be no requirement to compensate for propellant evaporation in pressure vessels during the filling process in order to maintain the correct concentration of API and ensure that accurate and reproducible filling of API in to the canisters. Another key advantage stems from the avoidance of having to constantly monitor the homogeneity of a liquefied dispersion of API in propellant during manufacture and filling of suspensions.

Particularly preferred disintegrants, ideally used as coatings, are menthol and propylene glycol (PG).

Most expressly preferred excipients are particulate carrier materials having a size range between range 15 μm-200 μm coated with disintegrants such as menthol or PG. Most ideally, said particulate carrier is lactose or leucine and it is, ideally, coated with menthol or PG.

According to a second aspect of the invention there is provided a tablet for use in the manufacture of a pMDI comprising:
i) a selected amount of at least one active particulate pharmaceutical ingredient (API);
ii) a disintegrant that is soluble in a liquid phase; and
iii) optionally, at least one excipient.

In yet a further preferred embodiment of the invention said API is a micronised API.

In yet a further preferred embodiment of the invention said API is soluble in the liquid phase.

Alternatively, or additionally, said API is insoluble in the liquid phase.

In yet a further preferred embodiment of the invention said tablet comprises a plurality of APIs. Preferably, said tablet comprises a plurality of APIs soluble in the liquid phase or a plurality of APIs insoluble in the liquid phase.

Alternatively, said tablet comprises at least one, or a plurality of, API(s) soluble in the liquid phase and at least one, or a plurality of, API(s) insoluble in the liquid phase.

More preferably still, said API is a respiratory therapeutic. Yet more preferably, said therapeutic is for treating one or more of the following diseases or conditions locally in the lungs: asthma, bronchitis, COPD, chest infections. Additionally the API might be selected for its systemic action within the body e.g. for acute pain relief, migraine, disorders of hormonal imbalance and cardiovascular disease. The API or combination of APIs of the invention may also be administered orally or intra-nasally for local treatment of disease or for systemic action within the body.

In a preferred embodiment of the invention said excipient is a particulate carrier material. Preferred materials include those commonly used in pharmaceutical drug delivery systems, e.g. carbohydrates including sugars, mono-, di-, tri-, oligo-, polysaccharides and any physiologically acceptable derivatives, salts, solvates thereof and any mixtures thereof e.g. lactose, spray dried lactose. Other suitable particulate carrier materials include amino acids, di-, tri-, oligo-, polypeptides, proteins and any physiologically acceptable derivatives, salts, solvates thereof and mixtures thereof, e.g. leucine. Advantageously, because of their relatively large particle size (i.e. range 15 μm-200 μm) these carrier particles are not likely to penetrate into the lungs during use. Thus, preferred particulate carrier materials have a particle size in the range 15 μm-200 μm.

Thus, in yet a further preferred embodiment of the invention said excipient has a particle size in the range 15 μm-200 μm.

More preferably, said disintegrant is selected from the group comprising: menthol, propylene glycol (PG), polyvinylpolypyrrolidone (PVP), polyethylene glycol (PEG), glycerol, sodium bicarbonate, citric acid and a non-toxic essential oil.

More preferably, said excipient is coated with a disintegrant selected from the group comprising: menthol, propylene glycol (PG), polyvinylpolypyrrolidone (PVP), polyethylene glycol (PEG), glycerol, sodium bicarbonate, citric acid and non-toxic essential oils.

Particularly preferred coatings are menthol and propylene glycol (PG).

Most expressly preferred excipients are particulate carrier materials having a size range between range 15 μm-200 μm coated with menthol or PG. Most ideally, said particulate carrier is lactose or leucine and it is, ideally, coated with menthol or PG.

More preferably still, said tablet further comprises a lubricant such as sodium lauryl sulphate and/or magnesium stearate.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The Invention will now be described by way of example only with reference to the Examples below and to the following FIGURES wherein.

Figure 1:
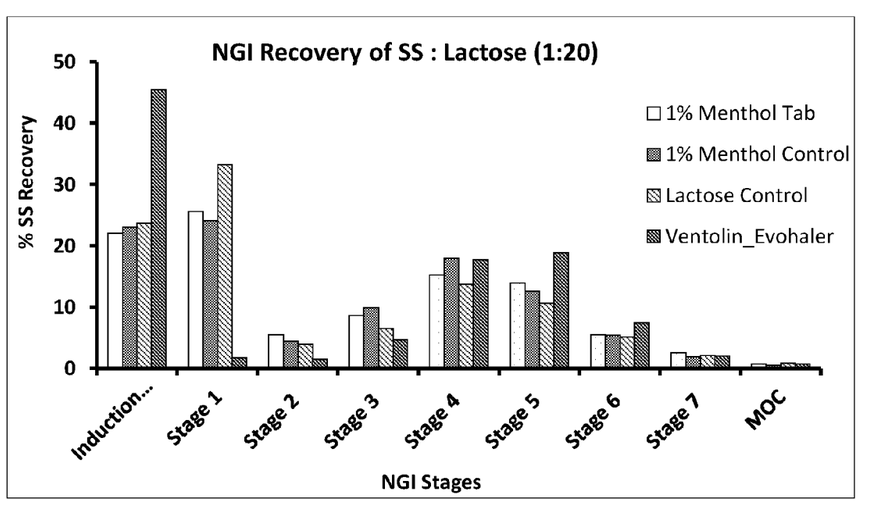
FIG. 1. Distribution Pattern of Recovered Salbutamol Sulphate (SS) (%) from the NGI for Test, Control and Reference Formulations.

Table 1. Solubility Estimates of Glycerol, Tween 80 and PEG 400 in HFA 134a.

Table 2. Solubility Estimates (Low Concentration) of Menthol, PVP, PEG 6000, PG, Sodium Bicarbonate and Citric Acid in Propellants 227 (*) and 134a (#).

Table 3. Solubility Estimates (High Concentration) of Menthol, PVP, and PG in Propellant 227 (*) and 134a (#).

Table 4. Theoretical Concentrations (% w/w) of Additive Coated onto Lactose Samples.

Table 5. Theoretical Concentrations (% w/w) of Salbutamol Sulphate Combined with Coated Lactose Samples (excipient and disintegrant) and Uncoated Lactose Control.

Table 6. Content Uniformity Data for Coated (excipient and disintegrant) and Uncoated (excipient—Control) SS:Lactose Samples.

Table 7. pMDI Formulations Used for Aerosol Testing. Test formulation=Lactose coated with 1% w/w Menthol Compressed into Tablet (excipient and disintegrant) (*). Control Formulation=Lactose Coated with 1% w/w Menthol Uncompressed (excipient and disintegrant) (#). Control Formulation=Uncoated Lactose Uncompressed (§) (excipient only).

Table 8. Summary of Aerosol Characteristics Using 0.35 mm Actuator Orifice Diameter. Test Formulation=Lactose Coated with 1% w/w Menthol Compressed into Tablet (excipient and disintegrant) (*). Control Formulation=Lactose Coated with 1% w/w Menthol Uncompressed (excipient and disintegrant) (#). Control Formulation=Uncoated Lactose Uncompressed (excipient only)-(§). FPF refers to the fine particle fraction, i.e. the % recovered API with a particle size less than 5 μm. FPD refers to the fine particle mass i.e. the mass of recovered API with a particle size less than 5 μm. MMAD refers to the mass median aerodynamic diameter, and GSD refers to the geometric standard deviation of the particle size distribution.

Table 9. Summary of Percentage Recovery of SS from the NGI for Test Formulation (*; Lactose Coated with 1% w/w Menthol Compressed into Tablet—excipient and disintegrant), 1% Menthol Control (#; lactose coated with 1% w/w Menthol uncompressed—excipient and disintegrant), Lactose Control (§; uncoated lactose (excipient) Uncompressed i.e. no disintegrant) and Reference Formulations (Commercial Ventolin® Evohaler Product). ECD refers to effective cut-off diameter (μm). MOC refers to Micro orifice collector.

Table 10. Theoretical Concentrations (% w/w) of Salmeterol Xinafoate and Fluticasone Propionate Combined with Coated Lactose Samples.

Table 11. Content Uniformity Data for Coated and Uncoated 1:8.6(SX)/2.5(FP):Lactose Samples.

Table 12. Content Uniformity Data for Coated and Uncoated 1:17.2(SX)/5(FP):Lactose Samples.

Table 13. Salmeterol xinafoate (SX):Fluticasone Propionate (FP) Combination Formulations Containing Lactose used for Aerosol Testing. The ratios (weight:weight) for API:lactose were 1:8.6 for SX and 1:2.5 for FP (*Control Formulation=Uncoated Lactose compressed into tablet; #Test Formulation=Lactose coated with 1% w/w Menthol compressed into tablet; ¥Control Formulation=Lactose coated with 1% w/w Menthol uncompressed).

Table 14. Salmeterol xinafoate (SX):Fluticasone Propionate (FP) Combination Formulations Containing Lactose Used for Aerosol Testing. The ratios (weight:weight) for API:lactose were 1:17.2 for SX and 1:5 for FP (*Control Formulation=Uncoated Lactose compressed into tablet; #Test Formulation=Lactose coated with 1% w/w Menthol Compressed into Tablet; ¥Control Formulation=Lactose coated with 1% w/w Menthol Uncompressed).

Table 15. Summary of Aerosol Characteristics of Salmeterol xinafoate from a Salmeterol xinafoate (SX):Fluticasone Propionate (FP) Combination Formulation Containing Lactose. The ratios (weight:weight) for API:lactose were 1:8.6 for SX and 1:2.5 for FP. Testing was performed using a 0.25 mm Actuator Orifice Diameter (Mean values n=3, ±SD).

Table 16. Summary of Aerosol Characteristics of Fluticasone Propionate from a Salmeterol xinafoate (SX):Fluticasone Propionate (FP) Combination Formulation Containing Lactose. The ratios (weight:weight) for API:lactose were 1:8.6 for SX and 1:2.5 for FP. Testing was performed using a 0.25 mm Actuator Orifice Diameter (Mean values n=3, ±SD).

Table 17. Summary of Aerosol Characteristics of Salmeterol xinafoate from a Salmeterol Xinafoate (SX):Fluticasone Propionate (FP) Combination Formulation Containing Lactose. The ratios (weight:weight) for API:lactose were 1:17.2 for SX and 1:5 for FP. Testing was performed using a 0.25 mm Actuator Orifice Diameter (Mean values n=3, ±SD).

Table 18. Summary of Aerosol Characteristics of Fluticasone Propionate from a Salmeterol xinafoate (SX):Fluticasone Propionate (FP) Combination Formulation Containing Lactose. The ratios (weight:weight) for API:lactose were 1:17.2 for SX and 1:5 for FP. Testing was performed using a 0.25 mm Actuator Orifice Diameter (Mean values n=3, ±SD).

Table 19. Summary of Content Uniformity Illustrating Recovery (%) of BDP from BDP:Lactose Powder Blends (1:2 and 1:5 weight in weight blends of BDP and Lactose)

Table 20. Summary of Dose Characteristics of BDP Solution Formulations (0.4 mm actuator orifice diameter). Test tablets were prepared from 1:5 BDP:Lactose blends (w/w) with lactose coated with 1% w/w menthol. Control tablets consisted of BDP with uncoated lactose. Additional controls included uncompressed powder formulations and BDP powder alone added directly to the HFA 134a: ethanol propellant system.

Table 21. Summary of Dose Characteristics of BDP Solution Formulations (0.25 mm actuator orifice diameter). These are the same test canisters as those described in Tables 24 and 25.

Table 22. Summary of Content Uniformity Illustrating Recovery (%) of BDP & SS from Lactose Powder Blends. The weight:weight (w/w) ratios for API:lactose were 1:12 for BDP and 1:5 for Salbutamol Sulphate.

Table 23. Summary of Dose Characteristics of BDP:SS Combination Formulations (0.25 mm actuator orifice diameter)—BDP Performance. The weight:weight (w/w) ratios for API:lactose were 1:12 for BDP and 1:5 for Salbutamol Sulphate. Test tablets were prepared from lactose coated with 1% w/w menthol. Control tablets consisted of blends of the APIs with uncoated lactose.

Table 24. Summary of Dose Characteristics of BDP:SS Combination Formulations (0.25 mm actuator orifice diameter)—SS Performance. The weight:weight (w/w) ratios for API:lactose were 1:12 for BDP and 1:5 for Salbutamol Sulphate. Test tablets were prepared from lactose coated with 1% w/w menthol. Control tablets consisted of blends of the APIs with uncoated lactose.

DETAILED DESCRIPTION

Materials and Methods

Solubility of Potential Disintegrants

The solubility of some potential disintegrants was estimated by weighing samples directly into plastic coated glass aerosol bottles or clear polyethylene terephthalate (PET) aerosol vials, sealing with metering valves and filling a known amount of propellant (HFA 134a or HFA 227ea,) directly into the vials using laboratory scale pressure filling equipment. Samples of glycerol, Tween 80 and PEG (polyethylene glycol) 400 were investigated in propellant HFA 134a. Menthol, PVP (polyvinylpolypyrrolidone) (molecular weight 36,000), PEG 6000, PG (propylene glycol), and also citric acid and sodium bicarbonate which have potential disintegrant properties were investigated in both propellants i.e. HFA 134a and 227.

Coating Lactose Bulk Samples

Separate samples of lactose were coated with either 1% or 5% w/w glycerol, PEG 400 or Tween 80 or with 1% w/w Menthol, PVP (molecular weight 360,000), PEG 6000, or propylene glycol (PG,).

For the 1% w/w samples of disintegrant approximately 0.2 g of disintegrant was added to 19.8 g of lactose. For the 5% w/w samples of disintegrant approximately 1 g of disintegrant was added to 19 g of lactose.

The disintegrants were dissolved in absolute ethanol and coated onto the lactose as follows. The disintegrant was added to a glass screw cap jar (50 mL) and a small amount of ethanol sufficient to dissolve the disintegrant was added. Subsequently the lactose was slowly introduced in discrete amounts followed by vigorous shaking of the jar upon each addition of lactose. The process was repeated until all the lactose was added to the jar and, if necessary (to ensure good wetting and dispersion of the lactose), further ethanol was added. Care was taken to ensure that the minimal amount of ethanol was used (enough to allow effective shaking of the contents and therefore coating of the lactose with disintegrant). Following shaking the contents were transferred to a 2 L Pyrex beaker and dried on stirrer/hotplate and the powdered coated lactose was recovered and stored in plastic zip-lok bags.

Preliminary Tablet Formulation I—No API

Initial tablet testing was performed using lactose coated with either 1 or 5% w/w PEG 400, and either 1% w/w glycerol or Tween 80. Samples of lactose coated with these potential disintegrants were compressed into tablets using a bench top tabletting machine fitted with a caplet punch and die assembly. Tablets were individually manufactured with the compression force setting no greater than 60 KN. Samples of lactose alone were used as controls. Typical tablet weights were approximately 0.4 g.

Test Formulation 1—Salbutamol Sulphate (SS):Coated Lactose

Proof of concept was proved using SS as a model API to blend with the coated lactose. Micronised SS was blended with coated lactose so that the final product contained approximately 5% w/w SS. Batch sizes were approximately 9.45 g total powder. Samples of the treated lactose were blended with the SS by passing through a 90 μm test sieve and transferred to a glass mortar. Thereafter the remaining coated lactose was added to the mortar so as to ensure geometric dilution of the mortar contents, which were mixed with a spatula. The powder blend was transferred to a stainless steel screw cap jar, secured in a low shear mixer and tumbled for 10 min at 46 rpm.

Batches were prepared in this way with lactose coated with 1% w/w menthol, PVP and PG.

Test Formulation 2—Combination of Insoluble APIs Salmeterol Xinafoate and Fluticasone Propionate Salmeterol Xinafoate and Fluticasone propionate were selected as a model API combination to blend with the lactose (coated or uncoated). Lactose was blended with the APIs so that the final product contained 7.8% and 26.9% w/w SX and FP respectively in a 1:8.6 (SX)/1:2.5 (FP): Lactose formulation and 4.7% and 16.3% w/w SX and FP respectively in a 1:17.2 (SX)/5 (FP):Lactose formulation. The target dose was 36.3 μg of SX (25 μg salmeterol) and 125 μg of FP per actuation from the valve and 30.5 μg (21 μg salmeterol) SX and 110 μg of FP from the actuator, the metering valve volume was 50 μL.

Batch sizes were approximately 4.48 and 4.94 g total powder for 1:8.6 (SX)/1:2.5 (FP) and 1:17.2 (SX)/1:5 (FP): Lactose formulations respectively. Samples of the coated lactose were blended with the SX:FP by adding discrete amounts of lactose to a glass mortar, and mixing with a spatula at each addition, to ensure geometric dilution of the APIs. The powder blend was transferred to a stainless steel screw cap jar, secured in a low shear mixer and tumbled for 10 min at 46 rpm.

1:8.6 (SX)/1:2.5 (FP) % w/w:Lactose tablets were manufactured using menthol coated lactose using a bench top tabletting machine fitted with a punch (upper and lower punch diameter 6 mm) and die (6.0 mm) assembly. Tablets were individually manufactured with uncoated and 1% coated lactose.

1:17.2 (SX)/1:5 (FP) % w/w:Lactose Tablets were individually manufactured with uncoated and 1% coated lactose.
Test Formulation 3-1:5 w/w BDP:Lactose (Control, Un-Coated Lactose)

Beclometasone Dipropionate (non-micronised) was selected as a model API to blend with the lactose both coated or uncoated. Lactose was blended with API so that the final product contained approximately 16.7% w/w BDP (approx 1:5 Lactose:BDP). The target dose was 50 μg of BDP per actuation, the metering valve volume was 50 μL.

Batch sizes were approximately 4.35 g total powder. Samples of the uncoated lactose were blended with the BDP by adding discrete amounts of lactose and BDP to a glass mortar, and mixing with a spatula at each addition, to ensure geometric dilution of the API. The powder blend was transferred to a stainless steel screw cap jar, secured in a low shear mixer and tumbled for 10 min at 46 rpm.

1:5 w/w BDP:Lactose compressed dosage forms were manufactured using uncoated lactose or 1% w/w menthol coated lactose using a bench top tabletting machine fitted with a punch and die assembly designed to produce 0.6 mm diameter round, flat face, bevelled edged tablets. Tablets were individually manufactured.

1:2 w/w BDP:Lactose was blended with the uncoated lactose so that the final product contained approximately 33.3% w/w BDP. Batch sizes were approximately 2.18 g total powder. Samples of the uncoated lactose were blended with the BDP in the same manner described for the 1:5 formulations. Coated formulations were repeated with the same bulk lactose coated with 1% w/w menthol.
Test Formulation 4—1:12 BDP:Lactose and Approx. 1:5 SS:Lactose)

BDP and micronised salbutamol sulphate were blended with uncoated lactose so that the final product contained approximately 5%, and 12% w/w BDP and SS respectively. Batch sizes were approximately 5.56 g total powder. Samples of the uncoated lactose were blended with the SS and BDP by passing through a 90 μm test sieve and transferred to a glass mortar and thoroughly mixed. Thereafter, the remaining uncoated lactose was added to the mortar so as to ensure geometric dilution of the mortar contents, which were mixed with a spatula. The powder blend was transferred to a stainless steel screw cap jar, secured in a low shear mixer and tumbled for 10 min at 46 rpm.
Content Uniformity The content uniformity of the powder blends was determined as follows: three samples were randomly taken from the bulk powder blends and accurately weighed into 100 mL flasks and diluted to volume with HPLC grade water. Following mixing, 50 μL samples were withdrawn and transferred to 10 mL volumetric flasks and diluted to volume. SS was quantified using a validated high performance liquid chromatography (HPLC) method. SX:FP, BDP, BDP/SS were quantified using a validated high performance liquid chromatography (HPLC) method.
Preliminary Disintegration Tests Samples of the tablets were individually weighed and dispensed into glass aerosol vials and 50 μL metering valves were crimped to seal the containers. HFA 134a was added in appropriate amounts via the valve and the weight of propellant dispensed into the can was recorded. In some cases the preparations were sonicated using a sonic bath or placed on a mechanical flask shaker. To facilitate more readily dispersed formulations, a ball bearing or plastic pea may be dispensed into the can during manufacture.
Preliminary Aerosol Testing—Particle Size Distribution Samples of the tablets prepared using 1% menthol coated lactose and blended with SS were used for aerosol testing. The tablets were dispensed into glass aerosol vials or PET vials, and 19 mL fluorocarbon polymerised aluminium canisters. 50 μL metering valves were crimped to seal the vials and propellant HFA 134a was filled.

In the case of soluble API formulations, the vial containing the tablet was placed into a mixture of dry ice/acetone in a Dewar flask along with pre-prepared canister of 5% (w/w) ethanol in HFA 134a propellant. Both the vial containing tablet and the canister containing the 5% ethanol in propellant HFA 134a were cooled in the dry ice/acetone mixture for at least 5 min. The canister of ethanol and propellant was securely clamped and the valve was removed, the contents were carefully poured into the pre-cooled can containing the tablet and the valve was placed on the can and without delay the valve was crimped securely in place.

In addition to the tablet preparations, powder blends (uncompressed controls) were investigated. For example, a sample of SS:coated lactose blend that had not been compressed into a construct, and the second was an equivalent ratio of SS:lactose in which the lactose had neither been coated nor compressed into a tablet.

The formulations and the control preparations were tested using actuators with 0.35 mm orifice diameters unless otherwise stated.

The aerodynamic particle size distribution of the emitted aerosols was determined by inertial impaction testing using a Next Generation Impactor (NGI) operated at a standard flow rate of 30 L/min. Recovered API samples were quantified by validated HPLC assay. One of the key aerosol characteristics determined from the NGI tests was the fine particle fraction (FPF), i.e. the % of the recovered API with an aerodynamic particle size less than 5 μm. It is generally regarded that particles with aerodynamic diameters of less than 5 μm will penetrate into the lower airways. Other key parameters evaluated from the NGI particle size distribution data were the fine particle dose (FPD) i.e. the amount (μg) of API with an aerodynamic particle size less than 5 μm.

Results

In order to investigate the feasibility of the proposed formulation approach a series of preliminary experiments were conducted to assess some of the key variables.

The strategy was to establish the solubility of proposed disintegrants in propellants HFA 134a and 227. Thereafter samples of lactose were coated with the most suitable disintegrant materials and compressed into tablets using a bench top tableting machine.

Following these experiments candidate disintegrants were coated onto lactose and blended with a model API i.e. salbutamol sulphate (SS). The powder blends were characterised in terms of content uniformity i.e. established that each unit dose of powder contained the calculated dose of SS.

Samples of the SS:coated lactose blends were compressed into tablets and dispensed into canisters and filled with propellant. Control samples consisted of the same powder blend dispensed into canisters without compaction into tablets, and also an equivalent SS:lactose blend with non-coated non-compressed lactose. The aerosol properties of these formulations were assessed and compared to a reference product i.e. Ventolin® (Evohaler, GSK, UK).

Solubility Results

Table 1 shows the observations relating to visual estimates of the solubility of glycerol, Tween 80 and PEG 400 in HFA 134a. It was determined that glycerol at a concentration of 0.063% w/w was not soluble in HFA 134a alone. The other materials at the low concentrations investigated were soluble.

Table 2 shows the observations relating to the solubility of other potential disintegrants in propellants 134a and 227. Menthol and PG appeared soluble in both propellants at the concentrations investigated. PVP was observed to be soluble in HFA 227 but not in HFA 134a. PEG 6000, sodium bicarbonate and citric acid were insoluble in both propellants at the concentrations investigated but are likely to be soluble in ethanol blends of the propellant.

Further solubility tests were performed for Menthol, PVP and PG to determine solubility at higher concentrations. The results are shown in Table 3.

Lactose Coating

Based on the actual weights of lactose and disintegrant materials used in the coating process, the concentrations on a % w/w basis for the six materials (i.e. Glycerol, PEG 400, Tween 80, Menthol, PVP and PG) observed to have some solubility in HFA propellants are shown in Table 4.

Example 1

1.1 Preliminary Tablet Formulation I—No API

Based on the solubility observations in Table 1, preliminary tablet formulations were prepared using lactose coated with 5% w/w PEG 400, 1% w/w PEG 400, 1% w/w Tween 80 or 1% w/w glycerol. Uncoated lactose was used a as control.

The 5% PEG 400 formulations had a greater tendency to disintegrate in HFA 134a than the 1% PEG 400, which was more effectively dispersed than 1% Tween 80, which in turn was more effectively dispersed than 1% glycerol. Order of disintegration was therefore 5% PEG 400>1% PEG 400>1% Tween>1% glycerol. It was found that although vigorous hand shaking caused a small amount of dispersion that sonication (or ball bearing/plastic ‘pea’ agitation) was necessary to fully disperse the 5% PEG 400 tablet.

The lactose only formulation showed no sign of dispersion following prolonged sonication i.e. >15 min. Thus it may be concluded that distintegrants were therefore necessary for dispersal of tablets formulated from lactose alone.

Table 2 showed that menthol, PVP and PG also had some solubility in HFA 134a and/or 227. Table 3 showed that the greatest levels of solubility were observed for menthol. Tablet formulations were subsequently prepared with lactose coated with 1% w/w menthol, PVP, and PG.

The percent of disintegrant as a proportion of the weight of lactose carrier is shown in Table 4.

1.2 Tablet Formulations with Selected Disintegrants were Readily Dispersible

Samples of tablets containing lactose coated with 1% menthol were observed to be most readily re-dispersed upon addition of HFA 134a. Shaking by hand was sufficient to cause disruption of the dosage form while short sonication (3 min) was found to remove visible aggregates. The 1% PVP and PG formulations were not as readily disrupted although the PG dosage form dispersed to a greater extent that the PVP tablet. The formulations were placed on a mechanical flask shaker for 1 h but large aggregates remained in the PG and PVP formulations. The vials were sonicated for 3 minutes and the number and size of the aggregates was reduced, however more and bigger aggregates remained in the PVP sample compared to the PG sample.

Example 2

2.1 Test Formulation 1: Salbutamol Sulphate (SS):Coated Lactose

The formulations were designed to deliver approximately 100 μg of salbutamol base from the mouthpiece i.e. to enable comparison with a reference product Ventolin® Evohaler (GlaxoSmithKline, UK) i.e. a commercially available form of micronised salbutamol sulphate suspended in HFA 134a. Ventolin was tested using its standard actuator.

The theoretical concentrations of salbutamol sulphate (SS) in the blends manufactured with coated lactose are shown in Table 5. For the control sample, SS was blended with uncoated lactose. All other samples contain the same batch of lactose following coating with the specified additives.

Table 6 shows the content uniformity for powder blends prepared from SS and coated and uncoated (control) lactose samples. The actual measured SS content of the blends as determined by HPLC was compared to the theoretical content determined from the known masses of SS and lactose used for manufacture. The mean values were all within ±7% of the theoretical values.

The variability of the measured concentrations were all less than 3% RSD indicating homogeneous distribution of the SS with the lactose.

The same batches of lactose and SS were used for the manufacture of all blends.

2.2 Preliminary Aerosol Characterisation

Samples of tablets prepared from SS blended with lactose coated with 1% w/w menthol were dispensed into aerosol containers and HFA 134a was added. For control purposes pMDI were also prepared from a sample of the SS:coated lactose batch that had not been compressed into tablets, and a batch of SS prepared with uncoated lactose that was not compressed into tablets. All batches contained SS at a nominal concentration of 5% w/w relative to the lactose i.e. 1:20 weight:weight (w/w) SS:lactose.

The constituents of the manufactured pMDI are shown in Table 7. Following manufacture the pMDI vials containing the tablet formulations with 1% coated menthol were shaken vigorously by hand which caused initial significant disruption of the tablets. However, on close inspection some small aggregates were still visible in the pMDI vials, consequently the vials were sonicated for 3×3 min which appeared to effectively disrupt the aggregates. No such aggregates were observed for the two control formulations.

Initial testing of the samples indicated that there was a propensity for the valve stem/actuator of the pMDI to block after a small number of actuations.

However, the properties of the emitted aerosol were well suited to inhalation therapy with 42% of the emitted SS recovered in the respirable range i.e. <5 μm aerodynamic diameter (Table 8). In terms of FPF (43%) the performance of the control formulations prepared from coated lactose was very similar to the novel formulation approach.

The mean emitted doses for the novel formulation and the uncoated lactose control were close to the theoretical values. The SS recovery from the coated lactose control was greater than the theoretical value.

The recovery of SS and the deposition pattern of SS in the NGI for the test formulation (compressed SS:menthol coated lactose), the control formulations (uncompressed SS:menthol coated lactose, and SS:uncompressed, uncoated lactose) and the reference product (Ventolin® Evohaler) are shown in Table 9 and FIG. 1.

Ventolin® Evohaler was tested alongside the novel formulation and control samples. In general there was good agreement between the FPF and FPD for test and reference products. The API recovery from the Induction Port and Stage 1 for the novel formulation was close to that recovered from the Induction Port for the Ventolin® reference product. The fraction of API recovered from Stages 4, 5 and 6 for the novel formulation showed a similar distribution to that of the Reference product.

Example 3

3.1 Test Formulation 2—Salmeterol Xinafoate and Fluticasone Propionate

Propellant disintegratable compressed dosage forms (tablets) containing a combination of two propellants (where propellant is specified earlier as being a blend or contain ethanol or other acceptable excipients), insoluble API's namely, fluticasone propionate (FP) and salmeterol xinafoate (SX), were prepared and used to formulate pressurised metered dose inhalers. Such combinations of a bronchodilator and an anti-inflammatory agent are commonly used in the therapy of asthma and COPD.

The formulations were designed to deliver approximately 36.3 μg of SX and 125 μg of FP per metered dose (120 doses) i.e. to be comparable with the Seretide® Evohaler® (Reference product, Glaxo Wellcome UK Limited, UK) a commercially available suspension form of salmeterol xinafoate and fluticasone propionate in HFA 134a. Seretide was tested using its standard actuator.

The theoretical concentrations of SX and FP in the blends manufactured with coated lactose are shown in Table 10. For the control sample SX and FP was blended with uncoated lactose.

Tables 11 and 12 show the content uniformity for powder blends prepared from SX:FP and coated and uncoated lactose samples. The actual measured SX:FP content of the blends as determined by HPLC was compared to the theoretical content determined from the known masses of SX:FP and lactose used for manufacture. The mean values were all within ±4% of the theoretical values.

The variability of the measured concentrations were all less than 3% RSD indicating homogeneous distribution of the SX:FP with the lactose.

The same batches of lactose, SS and FP were used for the manufacture of all blends.

3.2 Preliminary Tablet Characterisation

For the 1:8.6 (SX)/1:2.5 (FP) blends typical tablet weights were between 0.0633-0.0793 g for uncoated and 1% coated lactose formulations. The final theoretical menthol concentration in the pMDI canisters was from 0.0077-0.0083% w/w for 1% w/w menthol coated lactose formulations. Further details of these formulations are shown in Table 13.

For the 1:17.2(SX)/1:5(FP) blends typical tablet weights were between 0.1126-0.1227 g for uncoated and 1% coated lactose formulations. The final theoretical menthol concentration in the pMDI canisters was 0.0131-0.0137% w/w for 1% w/w menthol coated lactose formulations. Further details of these formulations are shown in Table 14.

3.3 Preliminary Aerosol Characterisation

Tables 15 and 16 show the dose characteristics for salmeterol and fluticasone respectively for formulations prepared from a blend of API and lactose with the following weight ratios 1:8.6 SX:lactose and 1:2.5 FP:lactose. Two control formulations were assessed, i.e. tablets prepared with uncoated lactose and also powder blends that were not compressed into tablets.

In general the tablets with lactose coated with disintegrant were more easily dispersed in the propellant than the uncoated control tablets. The control tablets even after hand shaking/mechanical shaking and sonication contained large agglomerates of powder.

Tables 15 and 16 show that the aerosol and dose characteristics i.e. FPF and FPD for both the SX and FP were in good agreement with the reference product (Seretide). The metered doses for these non-optimised novel formulations were also in line with the reference product.

The characteristics determined for the 1:8.6 SX:1:2.5 FP:lactose formulations were also observed for the 1:17.2 SX:1:5 FP:lactose formulations. Tables 17 and 18 summarise the aerosol and dose characteristics, the fine particle fractions and the fine particle doses delivered via the construct formulations compared favourably with the Reference Product.

Example 4

4.1 Test Formulation—Soluble API Beclometasone Dipropionate

Propellant disintegratable compressed dosage forms (tablets) containing a soluble API namely, Beclometasone Dipropionate (BDP), was prepared and used to formulate pressurised metered dose inhalers.

The formulations were designed to deliver approximately 50 μg of BDP per metered dose (200 doses) i.e. to be comparable with the QVAR® (Reference product, Teva UK Limited, UK) a commercially available solution form of beclomethasone dipropionate in HFA 134a. QVAR® was tested using its standard actuator.

Inspection of Table 19 illustrates the uniformity of the BDP:Lac powder blends. The RSD values of the powder blends were below 2% for all formulations. The BDP recoveries from the powder blends of the 1:2 coated and the 1:5 uncoated were approximately 112 and 85% respectively of the target. In the preparation of pMDI from these powder blends the mass of propellant added to the canisters was adjusted so as to provide 50 μg per actuation of BDP.

Typical construct weights for the 1:5 w/w BDP:Lactose blends were in the range 0.066-0.084 g. For the 1:2 w/w BDP:Lactose blends tablet weights ranged from 0.0401-0.0504 g.

4.2 Preliminary Aerosol Characterisation

BDP has a degree of solubility in HFA 134a, the extent of which makes suspension systems untenable due to the potential for API dissolution and subsequent crystal growth leading to unstable suspension systems. However, the addition of a small quantity of ethanol i.e. approx. 5% w/w is adequate to ensure sufficient solubility of BDP for at least 50 μg/actuation solution systems.

The dose characteristics and aerosol properties using an actuator with a 0.4 mm orifice diameter are shown in Table 20. Inspection of the PET vials for the BDP alone control formulation showed a clear solution indicating that the BDP was dissolved in the 5% w/w ethanol:HFA medium. For all formulations the majority of the BDP in the NGI (i.e. that not impacted in the Induction Port) was deposited on stages with effective cut-off diameters of less than 2.3 μm, with significant deposition below the micro-orifice collector (MOC<0.54 μm). This type of deposition pattern is indicative of an API being dissolved in the propellant system.

The dose characteristics and aerosol data shown in Table 21 were generated using the same pMDI units described above. However for these tests a 0.25 mm orifice diameter actuator was used. Consequently a finer and slower moving aerosol plume was generated i.e. reduced ballistic impaction. The aerodynamic particle size distribution of the novel formulations was shifted towards the right and was more closely aligned with that of the Reference product. Key aerosol parameters demonstrate this, in particular the FPF increased to match or exceed the Reference product.

Overall this provides proof of concept that following blending, non-micronised soluble API and lactose (coated and uncoated), can be compressed into tablet form and dispersed in a propellant system incorporating a co-solvent e.g. HFA 134a/ethanol blend, in which the soluble API subsequently dissolved. The dose properties and aerosol characteristics of the formulations were shown to compare favourably with marketed reference products.

Example 5

5.1 Test Formulation—Combination Soluble and Insoluble API

Soluble APIs may also be formulated in combination systems with insoluble suspended API, this is exemplified by the solution/suspension combination formulation of salbutamol sulphate (SS) and beclometasone dipropionate (BDP) where SS is in suspension and BDP is in solution.

Inspection of Table 22 illustrates the uniformity of the BDP/SS:Lac powder blends. The RSD values of the powder blends were below 2% for all formulations. Typical tablet weights were between 0.1771-0.1999 g and 0.0862-0.1038 g for uncoated and coated tablets respectively.

5.2 Preliminary Aerosol Characterisation

The dose characteristics and aerosol properties are shown in Tables 23 and 24.

The BDP data (Table 23) i.e. soluble API, show similar aerodynamic particle size distributions as QVAR®, resulting in fine particle fraction (range 70.70 81.12%<5 μm) values similar to the Reference product (72.96%<5 μm). The fine particle doses (range 32.26-35.74 μg) were also similar to that of QVAR® (26.54 μg).

Salbutamol sulphate data i.e. the suspended API, are shown in Table 24. Ventolin Evohaler (GSK) and Airomir (Teva) were assessed as the Reference products. Neither Reference formulation was an exact match for the Test formulation in that Ventolin does not contain any ethanol or other excipients, however the volume of the metered dose i.e. 50 μL matches that of the Test formulations. Whilst Airomir does contain ethanol it also has a surfactant (oleic acid) and utilises a smaller valve metering chamber (25 μL). Table 24 shows the metered doses (emitted doses) per actuation for these non-optimised formulations.

In general the fine particle fraction data (range 43.02-54.62%<5 μm) matched or exceeded those of the Reference products (range 36.01-48.80%<5 μm). As a consequence of the metered (emitted) dose exceeding the target the fine particle mass was also superior to the Reference products.

When actuated through a 0.25 mm diameter actuator orifice the aerosol so formed had characteristics similar to those observed for the two marketed products tested individually.

SUMMARY

Experiments to investigate the disintegration, in propellant HFA 134a, of tablets formed by the direct compression of lactose showed poor dispersion of the tablets. Consequently the solubility of a range of compounds identified as possible disintegrants i.e. materials to be included in the tablet that would promote dispersion in HFA propellants, were evaluated.

A range of materials i.e. glycerol, PEG 400, Tween 80, PVP and PG, showed limited solubility (approx. range 0.05-0.1% w/w) in HFA propellants. Menthol, in contrast was found to be soluble at concentrations of approx. 3% w/w in HFA 134a and 227.

Samples of lactose were coated with selected disintegrants at concentrations of either 1 or 5% w/w.

Since menthol showed the greatest solubility in the propellant this was identified as the material most likely to enhance disintegration of the compressed dosage forms.

Consequently menthol coated lactose was blended with a model API (SS) and compressed into tablets, dispensed into aerosol cans and metering valves crimped to seal the cans. Upon addition of propellant HFA 134a to the aerosol container the tablets were observed to disperse primarily by hand shaking, although ball bearings/plastic 'peas' or sonication was required to disrupt some small aggregates.

Following dispersion of the tablet the resulting suspension system within the aerosol container was expected to demonstrate similar properties to formulations described in the original PCT filing (3).

The key aerosol characteristics of this non-optimised test formulation compared favourably with the reference product (Ventolin® Evohaler). The concentration of menthol in terms of the propellant was very low i.e. approx. 0.4% % w/w (Table 7) thus it is anticipated that increasing the amount of menthol associated with the lactose may improve disintegration of the tablet. Solubility results show that the menthol concentration could be increased several-fold (see Table 3).

Additionally, it has been shown that both soluble and insoluble APIs can be prepared and delivered in this way.

Further, it has been shown that a combination of APIs can be effectively prepared and delivered and a dose equivalent to or greater than existing systems. This is particularly advantageous as it permits delivery of multiple therapeutics in a single controlled dose.

Additionally, it has been shown that two API's with differing physicochemical properties (i.e. micronised versus non-micronised) and differing therapeutic targets (i.e. anti-inflammatory versus bronchodilator) can be successfully blended together and compressed into a tablet, and importantly, dispersed without the need for mechanical shaking or sonication. Additionally, formulations prepared without disintegrant were also shown to disperse and the suspension/solution systems so formed demonstrated acceptable aerosol properties. This provides the ability to prepare both soluble and insoluble APIs in the preparation of pMDIs which previously proved troublesome.

Consequently, the technique disclosed herein could potentially greatly simplify the filling process by removing the requirement to perform complex pressurised single stage fills i.e. re-cycling homogenised suspension of micronised API at high pressures. Also steps such as determining when the pressure vessel required topping up with propellant (to account for evaporation into the head space) and sampling re-circulating suspension to determine API levels would become obsolete.

REFERENCES

To be completed based on those references retained above.
1. U.S. Pat. No. 5,776,432.
2. WO 98/56349
3. WO 99/51205
4. WO 2008/053250

TABLE 1

| Vial | Material | Wt of Material (g) | Wt 134a (g) | Conc. Additive (% w/w) 134a | Soluble (Y/N/) |
|---|---|---|---|---|---|
| 1 | Glycerol | 0.00090 | 10.5334 | 0.009 | Y |
| 2 | Glycerol | 0.0067 | 10.5727 | 0.063 | N |
| 3 | Tween 80 | 0.00097 | 10.5842 | 0.009 | Y |
| 4 | Tween 80 | 0.0083 | 10.5607 | 0.079 | Y |
| 5 | PEG 400 | 0.0099 | 10.5703 | 0.094 | Y |
| 6 | PEG 400 | 0.0055 | 10.6284 | 0.052 | Y |

TABLE 2

| Vial | Material | Wt of Material (g) | Wt HFA (g) | Conc. Additive (% w/w) in Propellant | Soluble (Y/N) |
|---|---|---|---|---|---|
| *1 | Menthol | 0.0051 | 11.7946 | 0.0432 | Y |
| *2 | Menthol | 0.0174 | 11.9227 | 0.1457 | Y |
| *3 | PVP | 0.0062 | 11.9582 | 0.0518 | Y |
| *4 | PEG 6000 | 0.0103 | 12.0205 | 0.0856 | N |
| *5 | Na Bicarbonate | 0.0040 | 11.7518 | 0.0340 | N |
| *6 | Citric Acid | 0.0091 | 11.9981 | 0.0758 | N |
| *7 | PG | 0.0098 | 11.5224 | 0.0850 | Y |
| #8 | Menthol | 0.0070 | 10.7485 | 0.0651 | Y |
| #9 | PVP | 0.0063 | 10.8160 | 0.0582 | N |
| #10 | PEG 6000 | 0.1020 | 10.7120 | 0.9432 | N |
| #11 | Na Bicarbonate | 0.0066 | 10.9173 | 0.0604 | N |
| #12 | Citric Acid | 0.0071 | 10.9377 | 0.0649 | N |
| #13 | PG | 0.0093 | 10.9534 | 0.0848 | Y |

TABLE 3

| Vial | Material Description | Wt of Material (g) | Wt HFA(g) | Conc. Additive (% w/w) 134a | Observations |
|---|---|---|---|---|---|
| *1 | Menthol | 0.0941 | 9.8298 | 0.9482 | Soluble |
| *2 | Menthol | 0.3076 | 9.9939 | 2.9860 | Insoluble, thin crystals at interface adhering to vial |
| *3 | PVP | 0.0977 | 9.8169 | 0.9854 | Insoluble, wetted material creamed at interface |
| *4 | PVP | 0.2768 | 9.9776 | 2.6993 | As above |
| *5 | PG | 0.0974 | 9.7900 | 0.9851 | Insoluble droplets adhering to sides of vial |
| *6 | PG | 0.2930 | 10.0344 | 2.8371 | As above |
| #7 | Menthol | 0.1014 | 9.4114 | 1.0659 | Soluble |
| #8 | Menthol | 0.3233 | 8.7691 | 3.5557 | Insoluble, long thin needle like crystals |
| #9 | Menthol | 0.5103 | 7.7642 | 6.1671 | As above |
| #10 | PVP | 0.1100 | 9.5586 | 1.1377 | Insoluble, particles, tending to flocculate |
| #11 | PVP | 0.2971 | 7.2789 | 3.9216 | As above |
| #12 | PG | 0.1011 | 18.1890 | 0.5528 | Insoluble, droplets at interface |
| #13 | PG | 0.2966 | 9.7761 | 2.9446 | As above |
| #14 | PG | 0.4980 | 9.9361 | 4.7728 | As above |

TABLE 4

| Target Conc. (% w/w) | Glycerol (g) | PEG 400 (g) | Tween 80 (g) | Menthol (g) | PVP (g) | PG (g) | Lactose (g) | Actual Conc. (% w/w) |
|---|---|---|---|---|---|---|---|---|
| 1% | 0.2014 | — | — | — | — | — | 19.8000 | 1.02 |
| 5% | 1.0167 | — | — | — | — | — | 19.0453 | 5.34 |
| 1% | — | 0.2004 | — | — | — | — | 19.8146 | 1.01 |
| 5% | — | 1.0030 | — | — | — | — | 19.0000 | 5.28 |
| 1% | — | — | 0.2070 | — | — | — | 19.8300 | 1.04 |
| 5% | — | — | 0.9919 | — | — | — | 19.0074 | 5.22 |
| 1% | — | — | — | 0.1996 | — | — | 19.8010 | 1.00 |
| 1% | — | — | — | — | 0.2009 | — | 19.8022 | 1.00 |
| 1% | — | — | — | — | — | 0.2025 | 19.8068 | 1.01 |

TABLE 5

| Blend Details | SS (g) | Lactose (g) | % SS (w/w) |
|---|---|---|---|
| 1% Menthol | 0.4728 | 8.9939 | 4.99 |
| 1% PG | 0.4729 | 8.9947 | 4.99 |
| 1% PVP | 0.4723 | 9.0001 | 4.99 |
| Lactose (Control) | 0.4725 | 9.0008 | 4.99 |

TABLE 6

| Formulation Details | Sample Mass (g) | Theoretical SS (g) | Actual SS (g) | % Theoretical |
|---|---|---|---|---|
| 1% Menthol | 0.1987 | 0.0099 | 0.0095 | 95.81 |
| (Coated | 0.1711 | 0.0085 | 0.0083 | 97.04 |
| Lactose) | 0.1985 | 0.0099 | 0.0100 | 100.90 |
| Mean | | | | 97.92 |
| SD | | | | 2.65 |
| RSD | | | | 2.71 |
| 1% PG | 0.1917 | 0.0096 | 0.0097 | 101.51 |
| (Coated | 0.2039 | 0.0102 | 0.0103 | 101.16 |
| Lactose) | 0.2139 | 0.0107 | 0.0112 | 104.49 |
| Mean | | | | 102.39 |
| SD | | | | 1.83 |
| RSD | | | | 1.79 |
| 1% PVP | 0.2068 | 0.0103 | 0.0100 | 96.44 |
| (Coated | 0.2216 | 0.0111 | 0.0110 | 99.01 |
| Lactose) | 0.2476 | 0.0124 | 0.0122 | 98.56 |
| Mean | | | | 98.00 |
| Control | 0.3041 | 0.0152 | 0.0166 | 109.25 |
| (Uncoated | 0.3157 | 0.0157 | 0.0165 | 104.72 |
| Lactose) | 0.3065 | 0.0153 | 0.0166 | 108.31 |
| Mean | | | | 107.43 |
| SD | | | | 2.39 |
| RSD | | | | 2.23 |

TABLE 7

| Vial Number | Formulation Description | Wt of tablet (g) | Wt 134a (g) | Total Wt of Filled Formulation (g) | Conc. Lac (% w/w) 134a | Conc. Menthol (% w/w) 134a |
|---|---|---|---|---|---|---|
| *1 | 1% Menthol-Tab | 0.3295 | 9.1730 | 9.5029 | 3.4675 | 0.0358 |
| *2 | 1% Menthol-Tab | 0.4299 | 9.1532 | 9.5833 | 4.4860 | 0.0468 |
| *3 | 1% Menthol-Tab | 0.3907 | 9.2909 | 9.6821 | 4.0355 | 0.0419 |
| #4 | Control 1% Menthol | 0.3518 | 9.3789 | 9.3785 | 3.6154 | 0.0374 |
| #5 | Control 1% Menthol | 0.3391 | 9.5533 | 9.5530 | 3.4279 | 0.0354 |
| #6 | Control 1% Menthol | 0.4333 | 9.5715 | 9.5711 | 4.3309 | 0.0452 |
| §7 | Control Lac | 0.3025 | 9.4364 | 9.4361 | 3.1061 | — |
| §8 | Control Lac | 0.3062 | 9.3829 | 9.3826 | 3.1603 | — |
| §9 | Control Lac | 0.4125 | 9.4851 | 9.4847 | 4.1677 | — |

TABLE 8

| Formulation | *1% Menthol Tablet | #1% Menthol Control | §Lactose Control | Ventolin® Evohaler |
|---|---|---|---|---|
| Metered (Shot) Weight (mg) | 82.10 | 69.38 | 65.78 | 0.07 |
| Metered Dose/Actuation inc. Actuator (μg) | N/D | 179.71 | 132.39 | N/D |
| Emitted SS Per Actuation (ex Actuator) (μg) | 118.78 | 148.74 | 108.98 | 99.67 |
| SS FPF (% <5 μm) | 42.26 | 43.28 | 35.66 | 49.35 |
| SS FPD (μg <5 μm) (ex device) | 50.20 | 64.37 | 38.86 | 40.82 |

TABLE 9

| Formulation | *1% Menthol | #1% Menthol Control | §Lactose Control | Ventolin® Evohaler Reference |
|---|---|---|---|---|
| Induction Port | 22.13 | 23.08 | 23.70 | 45.37 |
| Stage 1 (ECD = 11.72 μm) | 25.62 | 24.07 | 33.25 | 1.73 |
| Stage 2 (ECD = 6.4 μm) | 5.48 | 4.47 | 3.97 | 1.49 |
| Stage 3 (ECD = 3.99 μm) | 8.69 | 9.89 | 6.54 | 4.66 |
| Stage 4 (ECD = 2.3 μm) | 15.31 | 17.96 | 13.73 | 17.75 |
| Stage 5 (ECD = 1.36 μm) | 13.97 | 12.63 | 10.69 | 18.81 |
| Stage 6 (ECD = 0.83 μm) | 5.50 | 5.45 | 5.12 | 7.43 |
| Stage 7 (ECD = 0.54 μm) | 2.56 | 1.92 | 2.14 | 2.06 |
| MOC | 0.74 | 0.53 | 0.87 | 0.69 |

TABLE 10

| Blend Details | SX (g) | FP (g) | Lactose (g) | % SX (w/w) | % FP (w/w) |
|---|---|---|---|---|---|
| 1:8.6(SX)/2.5(FP):Coated Lactose | 0.3498 | 1.2051 | 2.9227 | 7.81 | 26.91 |
| 1:17.2(SX)/5(FP):Coated Lactose | 0.2332 | 0.8030 | 3.9039 | 4.72 | 16.25 |

TABLE 11

| Formulation Details | Sample Mass (g) | Theoretical API (mg) | Actual API (mg) | Theoretical (%) |
|---|---|---|---|---|
| 1:8.6(SX)/:Un-coated Lactose | 0.0739 | 5.6546 | 5.4381 | 96.17 |
| | 0.0739 | 5.6546 | 5.6259 | 99.49 |
| | 0.0739 | 5.6546 | 5.5707 | 98.82 |
| Mean | | | | 98.06 |
| SD | | | | 1.71 |
| RSD | | | | 1.74 |
| 1:2.5(FP):Un-coated Lactose | 0.0739 | 19.4897 | 19.0798 | 97.85 |
| | 0.0739 | 19.4987 | 19.6694 | 100.88 |
| | 0.0739 | 19.4987 | 19.5955 | 100.50 |
| Mean | | | | 99.74 |
| SD | | | | 1.65 |
| RSD | | | | 1.65 |
| 1:8.6(SX)/:1% coated Lactose | 0.0739 | 5.6546 | 5.5788 | 98.66 |
| | 0.0739 | 5.6546 | 5.6090 | 99.19 |
| | 0.0739 | 5.6546 | 5.5899 | 98.86 |

TABLE 11-continued

| Formulation Details | Sample Mass (g) | Theoretical API (mg) | Actual API (mg) | Theoretical (%) |
|---|---|---|---|---|
| | Mean | | | 98.90 |
| | SD | | | 0.27 |
| | RSD | | | 0.27 |
| 1:2.5(FP):1% coated Lactose | 0.0739 | 19.4897 | 19.5370 | 100.20 |
| | 0.0739 | 19.4987 | 19.4349 | 99.67 |
| | 0.0739 | 19.4987 | 19.9922 | 102.53 |
| | Mean | | | 100.80 |
| | SD | | | 1.52 |
| | RSD | | | 1.51 |

TABLE 12

| Formulation Details | Sample Mass (g) | Theoretical SS (mg) | Actual SS (mg) | Theoretical (%) |
|---|---|---|---|---|
| 1:17.2(SX)/:Un-coated Lactose | 0.1227 | 5.6571 | 5.5221 | 97.61 |
| | 0.1227 | 5.6571 | 5.6826 | 100.45 |
| | 0.1227 | 5.6571 | 5.6099 | 99.17 |
| | Mean | | | 99.08 |
| | SD | | | 1.42 |
| | RSD | | | 1.43 |
| 1:5(FP):Un-coated Lactose | 0.1227 | 19.5072 | 19.3246 | 99.06 |
| | 0.1227 | 19.5072 | 19.9174 | 102.10 |
| | 0.1227 | 19.5072 | 19.8502 | 101.76 |
| | Mean | | | 100.98 |
| | SD | | | 1.66 |
| | RSD | | | 1.65 |
| 1:17.2(SX)/:1% coated Lactose | 0.1227 | 5.6571 | 5.6976 | 100.72 |
| | 0.1227 | 5.6571 | 5.7033 | 100.82 |
| | 0.1227 | 5.6571 | 5.6813 | 100.43 |
| | Mean | | | 100.65 |
| | SD | | | 0.20 |
| | RSD | | | 0.20 |
| 1:5(FP):1% coated Lactose | 0.1227 | 19.5072 | 20.1627 | 103.36 |
| | 0.1227 | 19.5072 | 20.1625 | 103.36 |
| | 0.1227 | 19.5072 | 20.2293 | 103.70 |
| | Mean | | | 103.47 |
| | SD | | | 0.20 |
| | RSD | | | 0.19 |

TABLE 13

| Vial | Formulation Description | Wt of Tablet (g) | Wt 134a (g) | Total wt of Filled Formulation (g) | Conc. Lac (% w/w)134a | Conc. Menthol (% w/w) 134a |
|---|---|---|---|---|---|---|
| 1 | 1:8.6(SX)/2.5(FP): Un-coated Lactose Tab | 0.0793 | 9.2047 | 9.2840 | 0.85 | |
| 2 | 1:8.6(SX)/2.5(FP): Un-coated Lactose Tab | 0.0633 | 9.0227 | 9.0860 | 0.70 | |
| 3 | 1:8.6(SX)/2.5(FP): Un-coated Lactose Tab | 0.0657 | 9.0526 | 9.1183 | 0.72 | |
| 4[#] | 1:8.6(SX)/2.5(FP): 1% Menthol Tab (Coated Lactose) | 0.0703 | 9.2559 | 9.3262 | 0.75 | 0.0077 |
| 5[#] | 1:8.6(SX)/2.5(FP): 1% Menthol Tab (Coated Lactose) | 0.0726 | 9.0401 | 9.1127 | 0.80 | 0.0081 |
| 6[#] | 1:8.6(SX)/2.5(FP): 1% Menthol Tab (Coated Lactose) | 0.0702 | 9.0305 | 9.1007 | 0.77 | 0.0079 |
| 7[¥] | 1:8.6(SX)/2.5(FP): 1% Menthol Cont (Coated Lactose) | 0.0738 | 9.0342 | 9.1080 | 0.81 | 0.0083 |
| 8[¥] | 1:8.6(SX)/1:2.5(FP): 1% Menthol Cont (Coated Lactose) | 0.0738 | 9.0285 | 9.1023 | 0.81 | 0.0083 |
| 9[¥] | 1:8.6(SX)/1:2.5(FP): 1% Menthol Cont (Coated Lactose | 0.0738 | 9.0536 | 9.1274 | 0.81 | 0.0082 |

TABLE 14

| Vial Number | Formulation Description | Wt of Tablet (g) | Wt 134a (g) | Total wt of Filled Formulation (g) | Conc. Lac (% w/w)134a | Conc. Menthol (% w/w) 134a |
|---|---|---|---|---|---|---|
| 1* | 1:17.2(SX)/1:5(FP): Un-coated Tab | 0.1171 | 9.2829 | 9.4000 | 1.25 | |
| 2[#] | 1:17.2(SX)/1:5(FP): 1% Menthol Tab (Coated Lactose) | 0.1195 | 9.2352 | 9.3547 | 1.28 | 0.0131 |

TABLE 14-continued

| Vial Number | Formulation Description | Wt of Tablet (g) | Wt 134a (g) | Total wt of Filled Formulation (g) | Conc. Lac (% w/w)134a | Conc. Menthol (% w/w) 134a |
|---|---|---|---|---|---|---|
| 3¥ | 1:17.2(SX)/1:5(FP): 1% Menthol Cont (Coated Lactose) | 0.1227 | 9.0568 | 9.1795 | 1.34 | 0.0137 |
| 4¥ | 1:17.2(SX)/1:5(FP): 1% Menthol Cont (Coated Lactose) | 0.1226 | 9.0542 | 9.1768 | 1.34 | 0.0137 |
| 5¥ | 1:17.2(SX)/1:5(FP): 1% Menthol Cont (Coated Lactose) | 0.1126 | 9.1201 | 9.2427 | 1.33 | 0.0136 |

TABLE 15

| | Uncoated Tablet | 1% Menthol Tablet | 1% Menthol Uncompressed Control | Seretide Evohaler ® |
|---|---|---|---|---|
| Metered (shot) Weight (mg) | 65.36 ± 2.73 | 64.34 ± 1.66 | 65.23 ± 0.49 | 72.92 ± 0.18 |
| Metered Dose/Actuation inc. Actuator (µg) | 47.04 ± 5.68 | 37.47 ± 3.37 | 38.90 ± 2.93 | 33.94 ± 4.06 |
| Emitted SX/Actuation (ex-Actuator) (µg) | 42.90 ± 6.36 | 33.52 ± 2.65 | 35.97 ± 2.69 | 28.96 ± 2.87 |
| SX FPF (% <5 µm) | 46.26 ± 1.83 | 64.09 ± 3.79 | 62.02 ± 0.19 | 53.27 ± 3.78 |
| SX FPD (µg <5 µm) | 19.92 ± 3.63 | 21.54 ± 2.88 | 22.31 ± 1.67 | 15.40 ± 1.37 |

TABLE 16

| | Uncoated Tablet | 1% Menthol Tablet | 1% Menthol Uncompressed Control | Seretide Evohaler ® |
|---|---|---|---|---|
| Metered (shot) Weight (mg) | 65.36 ± 2.73 | 64.34 ± 1.66 | 65.23 ± 0.49 | 72.92 ± 0.18 |
| Metered Dose/Actuation inc. Actuator (µg) | 160.74 ± 15.91 | 132.71 ± 11.38 | 139.02 ± 10.84 | 131.14 ± 17.69 |
| Emitted FP/Actuation (ex-Actuator) (µg) | 146.61 ± 18.50 | 118.44 ± 8.90 | 128.36 ± 9.89 | 112.34 ± 12.26 |
| FP FPF (% <5 µm) | 47.77 ± 1.33 | 63.20 ± 3.69 | 62.48 ± 0.87 | 53.18 ± 4.17 |
| FP FPD (µg <5 µm) | 70.20 ± 10.66 | 75.05 ± 9.69 | 80.13 ± 5.11 | 59.54 ± 4.99 |

TABLE 17

| | Uncoated Tablet | 1% Menthol Tablet | 1% Menthol Uncompressed Control | Seretide Evohaler ® |
|---|---|---|---|---|
| Metered (shot) Weight (mg) | 65.64 | 70.30 | 64.57 ± 0.63 | 72.92 ± 0.18 |
| Metered Dose/Actuation inc. Actuator (µg) | 40.51 | 40.49 | 45.03 ± 0.44 | 33.94 ± 4.06 |
| Emitted SS/Actuation (ex-Actuator) (µg) | 34.66 | 37.60 | 41.48 ± 0.47 | 28.96 ± 2.87 |
| SX FPF (% <5 µm) | 50.53 | 56.86 | 54.68 ± 1.48 | 53.27 ± 3.78 |
| SX FPD (µg <5 µm) | 17.51 | 21.38 | 22.68 ± 0.60 | 15.40 ± 1.37 |

TABLE 18

|  | Uncoated Tablet | 1% Menthol Tablet | 1% Menthol Uncompressed Control | Seretide Evohaler ® |
|---|---|---|---|---|
| Metered (shot) Weight (mg) | 65.64 | 70.30 | 64.57 ± 0.63 | 72.92 ± 0.18 |
| Metered Dose/Actuation inc. Actuator (μg) | 141.94 | 144.13 | 159.23 ± 0.86 | 131.14 ± 17.69 |
| Emitted SS/Actuation (ex-Actuator) (μg) | 121.38 | 133.84 | 146.50 ± 1.36 | 112.34 ± 12.26 |
| FP FPF (% <5 μm) | 50.51 | 54.68 | 53.22 ± 1.52 | 53.18 ± 4.17 |
| FP FPD (μg <5 μm) | 61.31 | 73.18 | 77.96 ± 1.94 | 59.54 ± 4.99 |

TABLE 19

| Sample Number | 1:2 - BDP:Lac Uncoated | 1:2 - BDP:Lac 1% Menthol Coated | 1:5 - BDP:Lac Uncoated | 1:5 - BDP:Lac 1% Menthol Coated |
|---|---|---|---|---|
| 1 | 102.38 | 111.92 | 85.90 | 100.23 |
| 2 | 99.57 | 112.66 | 86.54 | 97.69 |
| 3 | 103.41 | 109.90 | 83.81 | 101.23 |
| MEAN | 101.79 | 111.49 | 85.42 | 99.72 |
| SD | 1.99 | 1.43 | 1.43 | 1.83 |
| RSD | 1.95 | 1.28 | 1.67 | 1.83 |

TABLE 20

|  | BDP only Control | 1:5 Control Powder | 1:5 1% Methol Powder | 1:5 Control Tablet | 1:5 1% Menthol Tablet | QVAR® Mean |
|---|---|---|---|---|---|---|
| Metered (Shot) Weight (mg) | 63.82 | 62.12 | 63.14 | 62.94 | 61.50 | 60.35 |
| Metered Dose BDP/Actuation inc. Actuator (μg) | 71.44 | 61.66 | 66.28 | 53.14 | 56.17 | 43.99 |
| Emitted Dose BDP/Actuation (ex Actuator) (μg) | 63.90 | 55.37 | 58.63 | 48.07 | 49.27 | 36.35 |
| BDP FPF (% <5 μm) | 40.28 | 41.61 | 41.55 | 44.33 | 42.89 | 72.96 |
| BDP FPD (μg <5 μm) (ex device) | 25.74 | 23.04 | 24.36 | 21.31 | 21.13 | 26.54 |

TABLE 21

|  | BDP only | *1:5 Control Powder | *1:5 1% Menthol Powder | 1:5 Control Tablet | QVAR® Mean |
|---|---|---|---|---|---|
| Metered (Shot) Weight (mg) | 62.82 | 61.66 | 61.60 | 62.94 | 60.35 |
| Metered Dose BDP/Actuation inc. Actuator (μg) | 66.98 | 56.42 | 65.95 | 58.33 | 43.99 |
| Emitted Dose BDP/Actuation (ex Actuator) (μg) | 62.17 | 52.94 | 58.83 | 54.22 | 36.35 |
| BDP FPF (% <5 μm) | 79.49 | 82.15 | 67.72 | 80.86 | 72.96 |
| BDP FPD (μg <5 μm) (ex device) | 49.42 | 43.48 | 39.84 | 43.85 | 26.54 |

TABLE 22

|  | 1:12/(1:5) - BDP/SS:Lactose UnCoated | | 1:12/(1:5) - BDP/SS:Lactose 1% Menthol Coated | |
|---|---|---|---|---|
| Sample Number | SS | BDP | SS | BDP |
| 1 | 94.93 | 87.11 | 96.41 | 92.23 |
| 2 | 95.46 | 90.00 | 99.00 | 92.69 |
| 3 | 95.78 | 88.05 | 97.52 | 92.61 |
| Average | 95.39 | 88.38 | 97.64 | 92.51 |
| SD | 0.43 | 1.48 | 1.30 | 0.24 |
| RSD | 0.45 | 1.67 | 1.33 | 0.26 |

TABLE 23

| Canister Number | Uncoated Powder | 1% Menthol Coated Powder | Uncoated Tablet | Uncoated Tablet | 1% Menthol Coated Tablet | 1% Menthol Coated Tablet | QVAR ® Mean |
|---|---|---|---|---|---|---|---|
| Metered (Shot) Weight (mg) | 62.3 | 62.3 | 60.9 | 63.4 | 60.3 | 61.6 | 60.35 |
| Metered Dose BDP/Actuation inc. Actuator (µg) | 47.11 | 49.57 | 46.43 | 48.71 | 51.01 | 47.22 | 43.99 |
| Emitted Dose BDP/Actuation (ex Actuator) (µg) | 44.23 | 45.62 | 43.92 | 45.33 | 47.55 | 43.62 | 36.35 |
| BDP FPF (% <5 µm) | 75.20 | 70.70 | 81.12 | 78.85 | 70.47 | 68.90 | 72.96 |
| BDP FPD (µg <5 µm) (ex device) | 33.26 | 32.26 | 35.63 | 35.74 | 33.51 | 30.06 | 26.54 |
| % of BDP on Actuator | 6.11 | 7.96 | 5.41 | 6.94 | 6.80 | 7.61 | NR |

TABLE 24

| Canister Number | Uncoated Powder | 1% Menthol Coated Powder | Uncoated Tablet F12 | Uncoated Tablet F13 | 1% Menthol Coated Tablet F12 | 1% Menthol Coated TabletF13 | Ventolin ® SS Mean | Airomir ®SS Mean |
|---|---|---|---|---|---|---|---|---|
| Metered (Shot) Weight (mg) | 62.3 | 62.3 | 60.9 | 63.4 | 60.3 | 61.6 | 74.35 | 31.52 |
| Metered Dose SS/Actuation inc. Actuator (µg) | 142.60 | 165.49 | 168.89 | 157.63 | 155.91 | 160.25 | 131.11 | 122.30 |
| Emitted Dose SS/Actuation (ex Actuator) (µg) | 119.62 | 151.23 | 157.97 | 147.14 | 144.04 | 148.51 | 113.53 | 95.59 |
| SS FPF (% <5 µm) | 49.25 | 43.02 | 54.62 | 52.16 | 50.26 | 48.47 | 36.01 | 48.80 |
| SS FPD (µg <5 µm) (ex device) | 58.91 | 65.06 | 86.28 | 76.74 | 72.39 | 71.98 | 40.95 | 46.54 |
| % of SS on Actuator | 16.11 | 8.61 | 6.47 | 6.66 | 7.61 | 7.33 | 13.41 | 21.84 |

The invention claimed is:

1. A method for the manufacture of a pressurised metered dose inhaler (pMDI) comprising:
   i) compressing a selected amount of at least one particulate active pharmaceutical ingredient (API) into a tablet;
   ii) placing said tablet into a canister;
   iii) fixedly attaching a dispensing valve to said canister; and
   iv) dispensing a liquid phase into said canister.

2. The method according to claim 1 wherein the method is undertaken as a single process or there is an interval following steps i) and/or ii) and/or iii).

3. The method according to claim 1 wherein step iv) may occur before step iii).

4. The method according to claim 1 wherein said API is for treating one or more of the following diseases or conditions: asthma, bronchitis, COPD, chest infections, acute pain relief, migraine, disorders of hormonal imbalance and cardiovascular disease.

5. The method according to claim 1 wherein said API is soluble in the liquid phase.

6. The method according to claim 1 wherein said API is insoluble in the liquid phase.

7. The method according to claim 1 wherein a disintegrant and/or excipient is compressed into said tablet.

8. The method according to claim 1 wherein said liquid phase comprises a propellant and/or a low volatility solvent and/or a surfactant.

9. The method according to claim 1 wherein a selected amount of a plurality of APIs are compressed in said tablet.

10. The method according to claim 1 wherein a selected amount of at least one or a plurality of soluble APIs are compressed in said tablet and/or a selected amount of at least one or a plurality of insoluble APIs are compressed in said tablet.

11. The method according to claim 7 wherein said disintegrant is selected from the group comprising: menthol, propylene glycol (PG), polyvinylpolypyrrolidone (PVP), polyethylene glycol (PEG), glycerol, sodium bicarbonate, citric acid and a non-toxic essential oil.

12. The method according to claim 7 wherein said excipient is a particulate carrier material.

13. The method according to claim 12 wherein said excipient is a particulate carrier material having a size range between range 15 µm-200 µm.

14. The method according to claim 13 wherein said excipient is a carbohydrate selected from the group comprising: mono-, di, tri, oligo, polysaccharide and any physiologically acceptable derivative, salt, solvate thereof and any mixtures thereof; or an amino acid selected from the group comprising: di-, tri-, oligo-, polypeptide, protein and any physiologically acceptable derivative, salt, solvate thereof and mixtures thereof.

15. The method according to claim 7 wherein said excipient is coated with said disintegrant.

16. The method according to claim 7 wherein said excipient is coated with said disintegrant, said disintegrant being selected from the group consisting of: menthol, propylene glycol (PG), polyvinylpolypyrrolidone (PVP), polyethylene glycol (PEG), glycerol, sodium bicarbonate, citric acid and a non-toxic essential oil.

17. The method according to claim 16 wherein said disintegrant is menthol or propylene glycol (PG).

18. The method according to claim 17 wherein said excipient is lactose or leucine.

19. The method according to claim 18 wherein said excipient is lactose and said disintegrant is menthol.

20. The method according to claim 8 wherein said propellant is a hydrofluorocarbon.

21. The method according to claim 20 wherein said propellant is a hydrofluoroalkane (HFA).

22. The method according to claim 20 wherein said propellant is a hydrofluoroolefin.

23. The method according to claim 21 wherein said HFA is HFA 134a (tetrafluorethane) or HFA 227ea (heptafluoropropane) or mixtures thereof.

24. The method according to claim 8 wherein said liquid phase comprises at least 80% w/w and up to 99.99% w/w of said propellant.

25. The method according to claim 24 wherein said liquid phase comprises at least 90% w/w and up to 99.99% w/w of said propellant.

26. The method according to claim 1 wherein part i) further comprises compressing a lubricant/glidant into said tablet.

27. The method according to claim 1 wherein a disintegrant is coated onto said at least one API.

* * * * *